(12) United States Patent
Blumenthal et al.

(10) Patent No.: US 7,833,192 B2
(45) Date of Patent: Nov. 16, 2010

(54) DEVICE FOR DISPENSING SUBSTANCES

(75) Inventors: Tilman von Blumenthal, Lübeck (DE); Jochim Koch, Ratzeburg (DE); Götz Kullik, Lübeck (DE)

(73) Assignee: Drägerwerk Aktiengesellschaft, Lübeck (DE)

( * ) Notice: Subject to any disclaimer, the term of this patent is extended or adjusted under 35 U.S.C. 154(b) by 1669 days.

(21) Appl. No.: 10/995,910

(22) Filed: Nov. 23, 2004

(65) Prior Publication Data

US 2005/0197622 A1 Sep. 8, 2005

(30) Foreign Application Priority Data

Mar. 2, 2004 (DE) .................. 10 2004 010 062

(51) Int. Cl.
*A61M 29/00* (2006.01)
*A61M 1/00* (2006.01)
*B01L 3/02* (2006.01)

(52) U.S. Cl. .................. 604/96.01; 422/100; 604/151
(58) Field of Classification Search .................. 604/82, 604/89, 151; 424/402, 427, 405, 400, 424, 424/426, 440, 473; 222/212, 83, 94; 428/144, 428/147, 402; 422/65, 100
See application file for complete search history.

(56) References Cited

U.S. PATENT DOCUMENTS

| | | | | |
|---|---|---|---|---|
| 5,382,400 A * | 1/1995 | Pike et al. | .................. | 264/168 |
| 5,507,412 A * | 4/1996 | Ebert et al. | .................. | 222/63 |
| 5,697,132 A * | 12/1997 | DeCarbo et al. | ............. | 27/22.1 |
| 5,897,527 A * | 4/1999 | Tsukada | .................. | 604/82 |
| 5,958,186 A * | 9/1999 | Holm et al. | .................. | 162/115 |
| H2086 H * | 10/2003 | Amsler | .................. | 442/327 |
| 6,932,502 B2 * | 8/2005 | Childers et al. | .......... | 366/152.1 |
| 7,018,361 B2 * | 3/2006 | Gillespie et al. | ............ | 604/151 |
| 7,237,942 B2 * | 7/2007 | Childers et al. | .......... | 366/152.1 |
| 2006/0031099 A1 * | 2/2006 | Vitello et al. | .................. | 705/2 |

FOREIGN PATENT DOCUMENTS

| | | |
|---|---|---|
| DE | 43 20 365 A1 | 12/1994 |
| DE | 198 02 368 C1 | 8/1999 |
| EP | 0 826 386 B1 | 3/1998 |
| JP | 02299663 A * | 12/1990 |
| WO | WO9808884 * | 3/1998 |

* cited by examiner

*Primary Examiner*—Nicholas D Lucchesi
*Assistant Examiner*—Ian K Holloway
(74) *Attorney, Agent, or Firm*—McGlew and Tuttle, P.C.

(57) ABSTRACT

A drug dispensing system is provided that may be used universally and in which medical substances can be mixed with a carrier solution (13) in a simple manner. The device and system have a dispensing module (6) for medical substances and a hydrophilic nonwoven (14) with a carrier solution (13). The emission area of substance discharge openings (21, 22, 23, 24) of the dispensing module (6) are directed toward the nonwoven (14).

20 Claims, 2 Drawing Sheets

DEVICE FOR DISPENSING SUBSTANCES

CROSS REFERENCE TO RELATED APPLICATIONS

This application claims the benefit of priority under 35 U.S.C. §119 of German patent application DE 10 2004 010 062.4 filed Mar. 2, 2004 the entire contents of which are incorporated herein by reference.

FIELD OF THE INVENTION

The invention relates to a drug dispensing system with a dispensing module for medical substances and a process for dispensing liquid or particulate substances using a dispensing module.

BACKGROUND OF THE INVENTION

Infusion systems that are designed in the form of a multichannel dispensing system for dispensing different volumes of solutions are used to dispense medical substances. Individual dispensing syringes, which are filled with the solutions selected by the user, are inserted in such systems into syringe holders, wherein the pistons of the dispensing syringes are actuated by a motor drive in order to pump the individual solutions into an infusion line. A central control unit of the multichannel dispensing system monitors the rate of dispensing of the individual solution.

The drawback of the prior-art multichannel dispensing system is that the dispensing syringes are disposable articles for hygienic reasons and must be disposed of The motor drives, which actuate the pistons, must operate with high precision and are therefore expensive. Due to the limited overall size of multichannel dispensing systems, the volume of the dispensing syringes is limited. Emptied dispensing syringes must therefore be frequently removed and replaced with new ones. In addition, the dispensing rates of the solutions affect each other and high time constants must be accepted in case of a change of the dispensing rates. A multichannel dispensing system of the said type has become known from DE 43 20 365 A1.

Microdispensing devices, which are based on the direct displacement of the solution to be dispensed, are known from other fields of application. An essential component of microdispensing devices is a pressure chamber, which is partially limited by a displacer in the form of a flexible membrane. By actuating the displacer, the solution to be dispensed is drawn up from a reservoir and then ejected from the pressure chamber via a discharge opening. The suction phase is controlled now such that a small change in the volume of the pressure chamber per unit of time is set.

In contrast, a great change in volume per unit of time is generated during the phase of dispensing in order to dispense a defined volume of solution. Depending on the viscosity and the surface tension, solutions can be dispensed in the range between 0.01 µL and 0.1 µL with some microdispensing devices. A microdispensing device of this type has become known from DE 198 02 368 C1.

Certain medical substances, for example, antibiotics, have only a limited shelf life in the liquid form. Dry powdered drug dispensing devices, with which very fine particles of a powdered drug can be made available in predetermined doses, are known for dispensing powdered drugs. A device of this type has become known from EP 826 386 B1. The drug is delivered to the patient via the respiratory tract with the prior-art dry powdered drug dispensing device.

However, the prior-art microdispensing devices and the dry powdered drug dispensing devices are not suitable for delivering the drugs to a patient intravenously.

SUMMARY OF THE INVENTION

The basic object of the present invention is to provide a drug dispensing system that can be used universally and with which medical substances can be delivered to a patient intravenously in a simple manner.

In addition, a process for dispensing drop-shaped or particulate substances shall be provided.

According to the invention, a drug dispensing system is provided with a dispensing module for medical substances and a hydrophilic nonwoven element (nonwoven) with a carrier solution. The dispensing module has substance discharge openings with an area of emission directed toward the nonwoven.

According to another aspect of the invention, a process for dispensing liquid or particulate substances with a dispensing module includes delivering a carrier solution for taking up substances through a hydrophilic nonwoven. The emission area of the substance discharge openings of the dispensing module is directed toward the nonwoven.

The advantage of the present invention is essentially that a carrier solution taking up the medical substance is sent through a hydrophilic nonwoven material, wherein substance discharge openings of a dispensing module for the medical substances are directed toward the surface of the nonwoven. The nonwoven is designed such that it binds the carrier liquid independently from the gravitation and the surface of the nonwoven is wetted by the carrier solution by capillary action. As a result, a direct contact is established between the medical substances being dispensed and the carrier solution. The structure of the nonwoven, i.e., the capillarity, is designed such that the surface tension of the carrier solution is sufficient at the entire interface of the nonwoven to prevent air from entering the carrier solution. The pressure conditions on the surface of the nonwoven can be set in a simple manner such that the nonwoven and the dispensing module are enclosed by a gas-tight mixing chamber and a certain working pressure is set within the mixing chamber during dispensing. The nonwoven is located in a mixing channel, which is open toward the mixing chamber and the carrier solution flows through it. The nonwoven completely fills out the mixing chamber, so that the carrier solution must flow through the capillaries of the nonwoven. The maximum allowable pressure difference between the pressure in the mixing chamber and the hydrostatic pressure in the carrier solution is inversely proportional to the capillary diameter of the nonwoven and depends on the surface tension of the carrier solution.

The mixing channel with the nonwoven is advantageously arranged on the underside of the mixing chamber, and the dispensing module is located opposite on the top side of the mixing chamber. Thus, an intermediate air space, by which wetting of the dispensing module with the carrier solution is prevented, is present between the substance discharge openings of the dispensing module and the nonwoven.

Another advantage of the dispensing device described in the present invention is that the overall size of the reservoirs for the substances to be dispensed is not limited, unlike in the case of dispensing syringes of prior-art infusion systems, and the reservoir must therefore be replaced at long time intervals only.

Another advantage is that the dispensing device can be used independently from its position.

The dispensing module is advantageously designed as a particle dispenser for substances that are in the dry form or as a drop dispenser for liquid substances. It is also possible to arrange the particle dispenser and the drop dispenser in the form of a parallel dispenser on a common valve bank and to dispense in this manner different medical substances simultaneously and independently from one another.

The carrier solution is preferably a sodium chloride solution, a glucose solution, a Ringer's solution, a fat emulsion or a nutrient solution.

A delivery pump, which draws up the carrier solution from a reservoir via the nonwoven and pumps same into an infusion line leading to a patient, is arranged on the outflow side of the nonwoven to transport the carrier solution through the nonwoven.

The suitable nonwoven materials are advantageously glass fiber, polyethylene with hydrophilic plasma coating, polyolefin or polyester.

An exemplary embodiment of the present invention is shown in the drawings and will be explained in greater detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
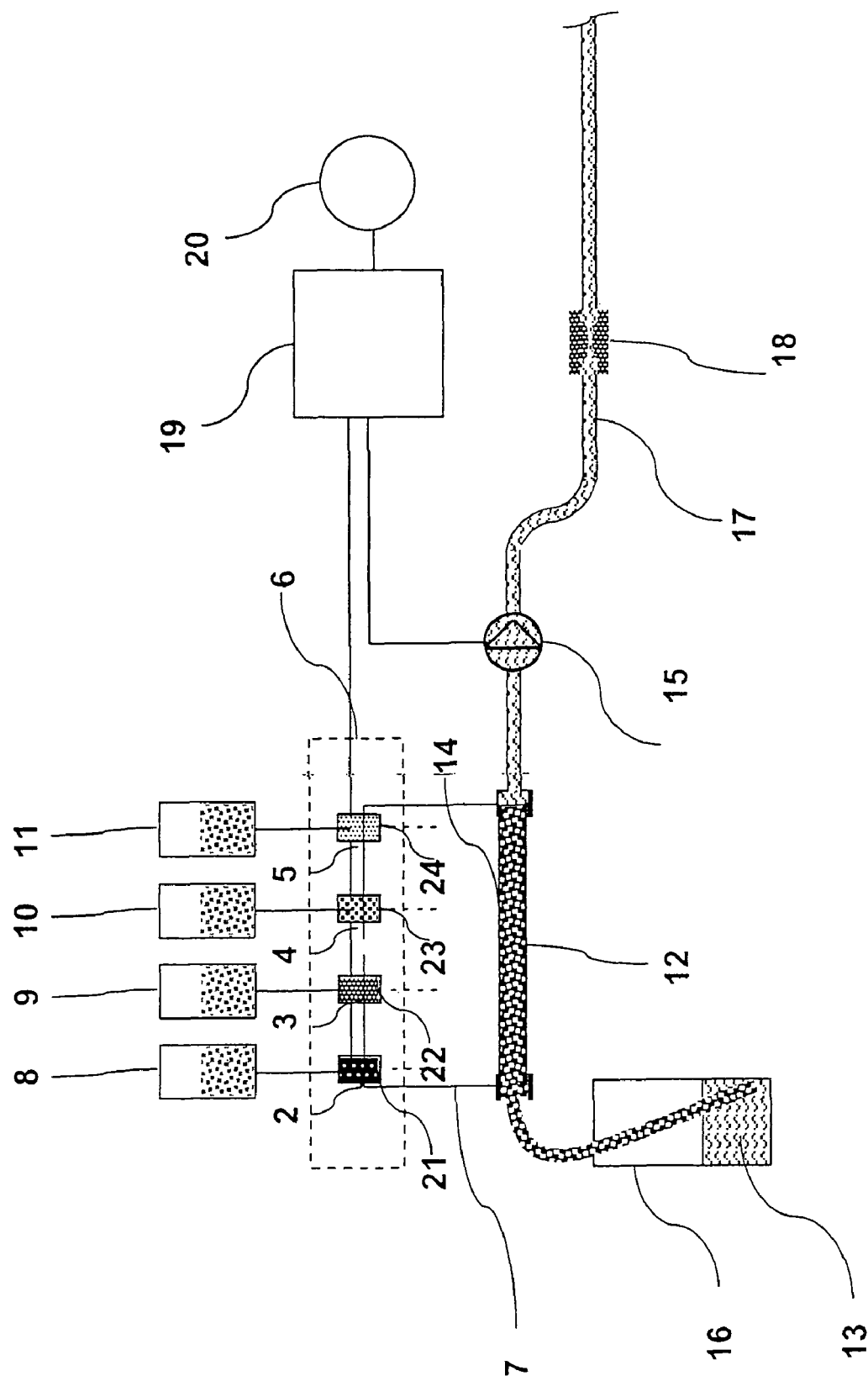
FIG. 1 is a schematic view of drug dispensing system according to the present invention.

A drug dispensing system 1 according to the present invention, which is shown in FIG. 1, contains two particle dispensers 2, 3 and two drop dispensers 4, 5, which together form a parallel dispenser 6 and are arranged on the top side of a mixing chamber 7. The particle dispensers 2, 3 are connected with reservoirs 8, 9, which contain drug powdered drugs, and two reservoirs 10, 11 filled with drug solutions are connected to the drop dispensers 4, 5. A mixing channel 12 arranged on the underside of the mixing chamber 7 is provided with a hydrophilic nonwoven 14 and contains a carrier solution 13. A delivery means 15 arranged on the outflow side of the mixing channel 12 draws in the carrier solution 13 via the nonwoven 14 from a reservoir 16 and pumps same into an infusion line 17, which is connected with a patient, not shown in FIG. 1. A defined delivery pressure is set in the infusion line 17 with a fluid resistor 18.

The particle dispensers 2, 3, the drop dispensers 4, 5 and the delivery means 15 are connected to a control unit 19, which performs all control and monitoring operations and generates control pulses for the dispensers 2, 3, 4, 5. The quantities of the substances to be dispensed can be set by means of an input unit 20 connected with the control unit 19.

The hydrophilic nonwoven 14 has a plurality of microstructured capillaries, which are wetted with the carrier solution 13. The particles or drops released by the dispensers 2, 3, 4, 5 via the substance discharge openings 21, 22, 23, 24 of these dispensers reach the surface of the nonwoven and are brought into contact there with the carrier solution 13 via the capillaries of the nonwoven 14. The pressure difference between the mixing chamber 7 and the mixing channel 12 must be set via the delivery means 15 such that no air will enter the mixing channel 12 from the mixing chamber via the capillaries of the nonwoven 14.

This relationship shall be explained on the basis of a numerical example.

The possible pressure difference is inversely proportional to the capillary diameter of the nonwoven 14. In case of a capillary diameter of 25 μm with a glass capillary in water, the pressure difference is approx. 116 mbar. Based on this parameter of the material, the pressure difference between the mixing chamber 7 and the mixing channel 12 must not exceed the value of 116 mbar.

Figure 2:
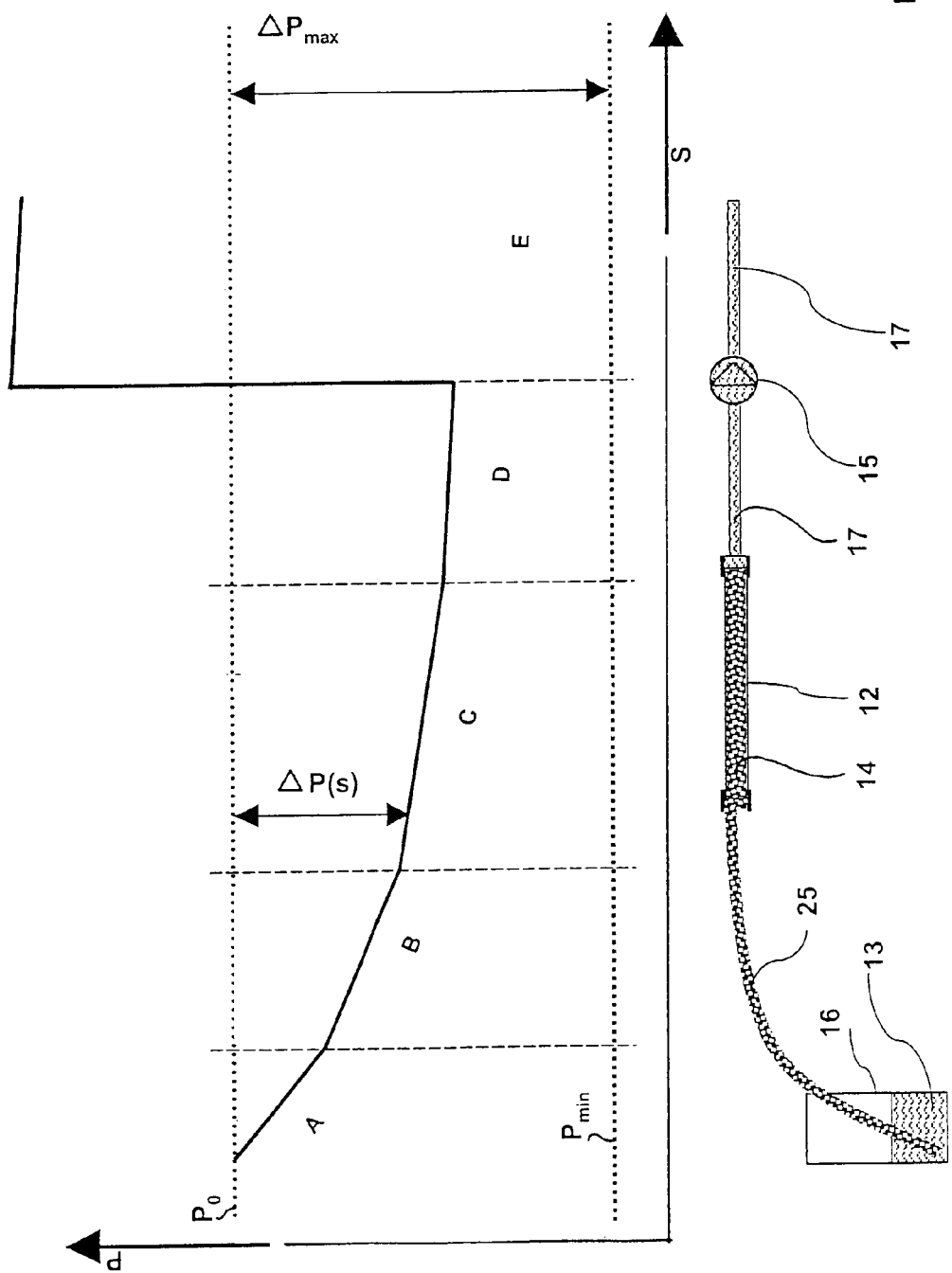
FIG. 2 is a schematic with a diagram showing the changes in the hydrostatic pressure along the flexible tube system transporting the carrier solution.

FIG. 2 illustrates the changes in the hydrostatic pressure p for the flexible tube system transporting the carrier solution 13 along the flow path s. The flow path s is divided into the sections A through E for the sake of greater clarity. The ambient pressure is $p_0$.

The carrier solution 13 is drawn in from the reservoir 16 via a hydrophilic wick 25. Based on the height difference between the liquid level of the carrier solution 13 and the wick 25, the hydrostatic pressure p drops below the ambient pressure $p_0$. The hydrostatic pressure p decreases by $\Delta p(s)$ in the sections B and C due to the resistance of the wick 25 and the resistance of the nonwoven 14 in the mixing channel 12. The flow resistor of the infusion line 17 is added to this in section D. The pressure conditions will then be reversed in the infusion line 17 due to the delivery means 15, so that the hydrostatic pressure p will be greater than the ambient pressure $p_0$ on the outflow side of the delivery means 15, in section E. The delivery means 15 must be set now such that the pressure will not drop below the pressure limit of $p_{min}$ and that a pressure difference of $\Delta p_{max}$ in the nonwoven 14 will not be exceeded in order to prevent air from passing through and into the carrier solution 13.

While a specific embodiment of the invention has been shown and described in detail to illustrate the application of the principles of the invention, it will be understood that the invention may be embodied otherwise without departing from such principles.

What is claimed is:

1. A drug dispensing system, comprising:
    a dispensing module for dispensing medical substances, the dispensing module having a discharge opening;
    a mixing channel comprising a hydrophilic nonwoven extending along a length thereof, said hydrophilic nonwoven having capillaries defining a fluid exchange interface, said mixing channel receiving a carrier solution via said hydrophilic nonwoven, wherein an area of emission of the medical substance from said discharge opening of said dispensing module is directed toward the nonwoven such that said hydrophilic nonwoven receives medical substances from said dispensing module, said capillaries of said hydrophilic nonwoven delivering medical substances to said carrier solution at said fluid exchange interface in said mixing channel such that said carrier solution mixes with said medical substances to form a medical fluid.

2. A drug dispensing system in accordance with claim 1, wherein said dispensing module comprises a particle dispensing means.

3. A drug dispensing system in accordance with claim 1, wherein said dispensing module comprises a drop dispenser means.

4. A drug dispensing system in accordance with claim 1, wherein said dispensing module comprises a parallel dispenser with a plurality of discharge openings located in an area of emission directed toward the nonwoven for dispensing different medical substances.

5. A drug dispensing system in accordance with claim 4, wherein said parallel dispenser is designed for the simultaneous and independent dispensing of drops of different substances and particles of different substances.

6. A drug dispensing system in accordance with claim 1, wherein said carrier solution is one of a sodium chloride solution, a glucose solution, a Ringer's solution, a fat emulsion or a nutrient solution.

7. A drug dispensing system in accordance with claim 1, said nonwoven comprises glass fibers, polyethylene with hydrophilic plasma coating, cellulose, polyolefin or polyester.

8. A drug dispensing system in accordance with claim 1, further comprising a delivery means for pumping the carrier solution into an infusion line and for setting a pressure such that a pressure difference between a barometric pressure in the emission area of the substance discharge and a hydrostatic pressure in said nonwoven is less than a maximum capillary pressure, said delivery means being provided on the outflow side of the nonwoven.

9. A process for dispensing liquid or particulate substances with a dispensing module, the process comprising the steps of:

providing a mixing channel having a hydrophilic nonwoven extending along a length thereof, said hydrophilic nonwoven having a capillary structure defining a fluid exchange interface of said mixing channel;

providing a reservoir of carrier solution upstream of said mixing channel;

directing an emission area of substance discharge openings of a dispensing module toward the nonwoven such that said capillary structure of said nonwoven receives substances from said dispensing module;

passing carrier solution from said reservoir of carrier solution to said mixing channel via said hydrophilic nonwoven such that said carrier solution receives said substances at said fluid exchange interface to form a medical fluid;

delivering said medical fluid intravenously to a patient.

10. A process in accordance with claim 9, wherein a delivery means for delivering the carrier solution is arranged downstream of the nonwoven.

11. A process in accordance with claim 9, wherein a pressure difference between the barometric pressure in the emission area of the substance discharge openings and the hydrostatic pressure in the nonwoven is set such that such pressure is lower than the maximum capillary pressure, the maximum capillary pressure being obtained from the pairing of the nonwoven and the carrier solution.

12. A drug dispensing system, comprising:

a dispensing module for dispensing medical substances, the dispensing module having a plurality of discharge openings;

a mixing channel having a hydrophilic nonwoven extending along a length thereof, said hydrophilic nonwoven having a capillary structure, said capillary structure defining a fluid exchange surface of said mixing channel;

a carrier solution container with carrier solution in said container and taken up by said nonwoven, said carrier solution container being located upstream of said mixing channel, said substance discharge openings of said dispensing module each having an area of emission directed toward said nonwoven in a region in which said carrier solution is taken up;

a pump transferring carrier solution from said carrier solution container through said mixing channel via said hydrophilic nonwoven such that said carrier solution mixes with said medical substances at said fluid exchange interface to form a medical fluid mixture, said pump transferring said medical fluid mixture from said mixing channel to a patient.

13. A drug dispensing system in accordance with claim 12, wherein said dispensing module comprises a particle dispensing means for dispensing substance particles at least at one of said substance discharge openings.

14. A drug dispensing system in accordance with claim 12, wherein said dispensing module comprises a drop dispenser means for dispensing liquid substance at least at one of said substance discharge openings.

15. A drug dispensing system in accordance with claim 12, wherein said dispensing module comprises a parallel dispenser means corresponding with said plurality of discharge openings for dispensing different medical substances.

16. A drug dispensing system in accordance with claim 15, wherein said parallel dispenser means is for the simultaneous and independent dispensing of drops of different substances and/or particles of different substances.

17. A drug dispensing system in accordance with claim 12, wherein said carrier solution is one of a sodium chloride solution, a glucose solution, a Ringer's solution, a fat emulsion or a nutrient solution.

18. A drug dispensing system in accordance with claim 12, wherein said nonwoven comprises glass fibers, polyethylene with hydrophilic plasma coating, cellulose, polyolefin or polyester.

19. A drug dispensing system in accordance with claim 12, wherein said pump transfers said medical fluid mixture to the patient through an infusion line, said pump transferring said carrier solutions from said carrier solution container through said mixing channel to said infusion line such that air does not enter said mixing channel via said capillary structure of said nonwoven, said pump maintaining a pressure in said mixing channel such that a pressure difference between a barometric pressure in the emission area of the substance discharge and a hydrostatic pressure in said nonwoven is less than a maximum capillary pressure.

20. A drug dispensing system in accordance with claim 1, further comprising:

a carrier solution container having a reservoir of said carrier solution, said carrier solution container being located upstream of said mixing channel, said mixing channel having a hydrophilic wick integrally connected thereto, said hydrophilic wick extending into said reservoir of said carrier solution;

a mixing chamber comprising said dispensing module and said mixing channel;

a delivery means for transferring said carrier solution from said carrier solution container through said mixing channel via said hydrophilic wick and said hydrophilic nonwoven to an infusion line such that air does not enter said mixing channel from said mixing chamber via said capillaries of said nonwoven.

* * * * *